US008152709B2

(12) United States Patent
Szeto

(10) Patent No.: US 8,152,709 B2
(45) Date of Patent: Apr. 10, 2012

(54) MAGNETIC THERAPEUTIC PAD FOR A HUMAN SPINE

(75) Inventor: Chik Szeto, Wan Chai (HK)

(73) Assignee: Lead-Setter Co. Limited, Wanchai (HK)

( * ) Notice: Subject to any disclaimer, the term of this patent is extended or adjusted under 35 U.S.C. 154(b) by 22 days.

(21) Appl. No.: 12/550,851

(22) Filed: Aug. 31, 2009

(65) Prior Publication Data

US 2010/0056848 A1 Mar. 4, 2010

(30) Foreign Application Priority Data

Sep. 1, 2008 (HK) .................................. 08109664

(51) Int. Cl.
*A61N 1/00* (2006.01)

(52) U.S. Cl. ............................................. 600/15; 600/9

(58) Field of Classification Search ................ 600/9, 15, 600/10–14; 5/633–635, 652–657.5, 733, 5/906; 606/240
See application file for complete search history.

(56) References Cited

U.S. PATENT DOCUMENTS

| 2,373,421 | A | * | 4/1945 | Schenker | 5/244 |
| 3,359,577 | A | * | 12/1967 | Rogers | 5/630 |
| 4,509,219 | A | * | 4/1985 | Yagi | 5/693 |
| 5,161,272 | A | * | 11/1992 | Yamaguchi et al. | 5/693 |
| 5,207,704 | A | * | 5/1993 | Shields | 606/240 |
| 6,267,719 | B1 | * | 7/2001 | Grisoni et al. | 600/15 |

FOREIGN PATENT DOCUMENTS

CN 2588956 Y 12/2003

\* cited by examiner

*Primary Examiner* — Charles A Marmor, II
*Assistant Examiner* — Carrie R Dorna
(74) *Attorney, Agent, or Firm* — Yimei C. Hammond; Kremblas & Foster

(57) ABSTRACT

The present patent application is directed to a magnetic therapeutic pad for a human spine. The magnetic therapeutic pad includes a substrate layer and a support layer above the substrate layer. The support layer includes a plurality of ridge frames spaced with one another. Upper edges of the ridge frames protrude out from an upper surface of the substrate layer. A plurality of magnets are disposed on the upper edges of the ridge frames according to the human meridian system. The ridge frames respectively correspond to a Governor meridian, inner Urinary Bladder meridians, and outer Urinary Bladder meridians on a human's back. The upper edges of the ridge frames form a curvature that is compatible with a curvature of a human back.

15 Claims, 5 Drawing Sheets

MAGNETIC THERAPEUTIC PAD FOR A HUMAN SPINE

CROSS-REFERENCES TO RELATED APPLICATIONS

This application claims the benefit of Hong Kong Patent Application No. 08109664, filed on Sep. 1, 2008; the contents of which is hereby incorporated by reference.

STATEMENT REGARDING FEDERALLY-SPONSORED RESEARCH AND DEVELOPMENT (Not Applicable)

REFERENCE TO AN APPENDIX (Not Applicable)

BACKGROUND OF THE INVENTION

1. Field Of The Invention

The present invention generally relates to a health care device and more particularly to a magnetic therapeutic pad for a human spine that is capable of correcting spinal vertebrae misalignment/displacement and magnetically stimulating spinal and back meridians for a user.

2. Description Of The Related Art

Theories of traditional Chinese medicine state that the human body has natural patterns of energy flow (called "qi" in Chinese) that circulate in channels called meridians. Symptoms of various illnesses are often believed to be the product of disrupted, blocked, or unbalanced qi movement (interrupted flow) through the body's meridians, as well as deficiencies or imbalances of qi (homeostatic imbalance) in the various organs. Traditional Chinese medicine often seeks to relieve these imbalances by adjusting the circulation of qi (metabolic energy flow) in the body using a variety of therapeutic techniques. Some of these techniques include herbal medicines, special diets, physical training regimens (qigong, tai chi chuan, and other martial arts training), moxibustion, massage to clear blockages, magnetic stimulation, and acupuncture, which uses small diameter metal needles inserted into the skin and underlying tissues to reroute or balance qi.

The theory of acupuncture points and meridians is an integral part of the foundation of the traditional Chinese medical practice. According to this theory, the endless circulation of blood and "qi" through the meridian system in a human body is responsible for the maintenance of the human's health and life. In the 1980's, scientists in China and around the world have proved the existence of meridians in the human body by biophysical and physiological methods utilizing sound, light, electricity, heat and/or isotopes. It is known now that there are 14 major meridians in a human body, among which the Governor (called "Du" in Chinese) meridian runs on the spinal column and the inner and outer Urinary Bladder meridians run next to and along each side of the Governor meridian. The Governor meridian and the Urinary Bladder meridians together perform a vital function in regulation, nourishment and therapy of the organs of the entire human body and in maintaining the person's general health.

Acupuncture points, also called acupoints, are locations on the body that are the focus of acupuncture, acupressure, sonopuncture and laser acupuncture treatment. Several hundred acupuncture points are located along meridians (connected points across the anatomy which affect a specific organ or other part of the body).

BRIEF SUMMARY OF THE INVENTION

The present patent application is directed to a magnetic therapeutic pad for a human spine. The magnetic therapeutic pad includes a substrate layer and a support layer above the substrate layer. The support layer includes a plurality of ridge frames spaced with one another. Upper edges of the ridge frames protrude out from an upper surface of the substrate layer. A plurality of magnets are disposed on the upper edges of the ridge frames according to the human meridian system. The ridge frames respectively correspond to a Governor meridian, inner Urinary Bladder meridians, and outer Urinary Bladder meridians on a human's back. The upper edges of the ridge frames form a curvature that is compatible with a curvature of a human back.

N and S polarities of the magnets may be arranged on each of the ridge frames in an alternating fashion so that any two neighboring magnets on each of the ridge frames have opposite polarities.

The magnets are along a line perpendicular to the ridge frames have the same polarity.

The average distance between the neighboring protruding upper edges of each ridge frame is about 3 cm to about 5 cm. A width of each ridge frame is approximate to the width of human spinal vertebrae.

Each ridge frame may include a waist portion and a neck-chest portion. The highest point of the upper edges of the waist portion is the highest point of the whole ridge frame. The upper edges of the neck-chest portion of the ridge frame forms a line that is parallel to the surface of the substrate layer facing the support layer.

The height of the ridge frame at a center of the pad (the center ridge frame) is the lowest among all the ridge frames. The height of the ridge frames gradually increases from the center ridge frame toward the ridge frames at outer sides of the pad. The heights of the ridge frames at outer most sides of the pad are the highest among all the ridge frames.

The ridge frames may be arranged and fixed on the substrate layer in a way that their projections from the substrate layers are parallel to each other.

The magnetic therapeutic pad may include a buffer layer covered on the support layer.

The magnets respectively match acupuncture points on the meridians that the ridge frames correspond to when a user is lying on the magnetic therapeutic pad.

Each of the magnets may be disposed in a hole formed at a protruding upper edge of each ridge frame.

DETAILED DESCRIPTION OF THE INVENTION

Reference will now be made in detail to a preferred embodiment of the magnetic therapeutic pad for a human spine disclosed in the present patent application, examples of which are also provided in the following description. Exemplary embodiments of the magnetic therapeutic pad for a human spine disclosed in the present patent application are described in detail, although it will be apparent to those skilled in the relevant art that some features that are not particularly important to an understanding of the magnetic therapeutic pad for a human spine may not be shown for the sake of clarity.

Furthermore, it should be understood that the magnetic therapeutic pad for a human spine disclosed in the present patent application is not limited to the precise embodiments described below and that various changes and modifications thereof may be effected by one skilled in the art without departing from the spirit or scope of the protection. For example, elements and/or features of different illustrative embodiments may be combined with each other and/or substituted for each other within the scope of this disclosure.

Figure 1:
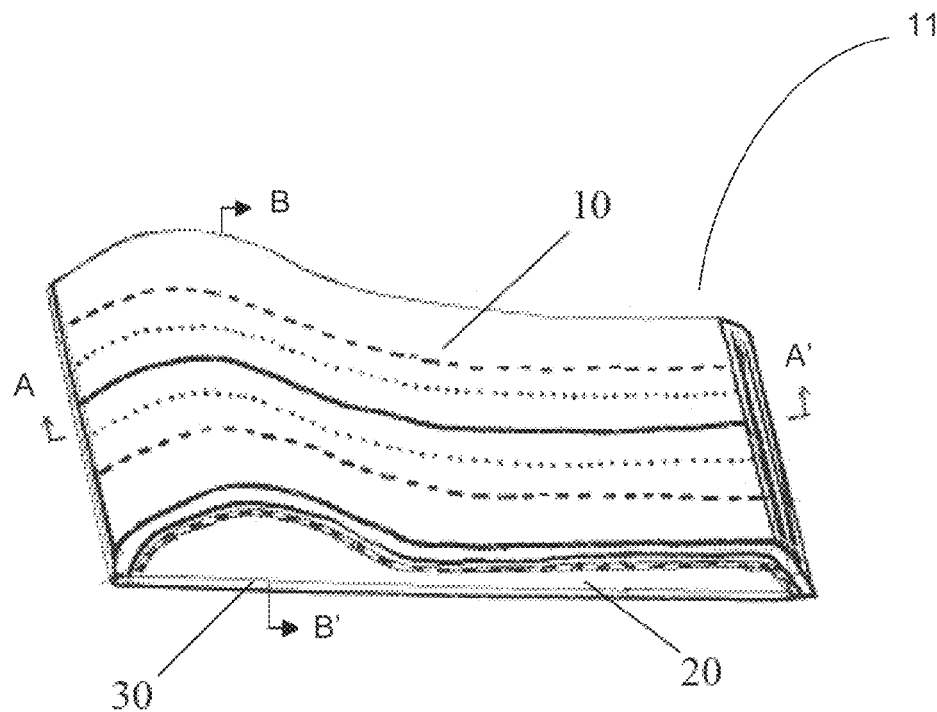
FIG. 1 is a perspective view of a magnetic therapeutic pad for a human spine according to an embodiment of the present patent application.

FIG. 1 is a perspective view of a magnetic therapeutic pad 11 for a human spine according to an embodiment of the present patent application. Referring to FIG. 1, the magnetic therapeutic pad for a human spine includes a substrate layer 30, a support layer 20 above the substrate layer 30, and a buffer layer 10 covered on the support layer 20. A package layer (not shown) made by leather or other suitable material may be configured to cover the outer surface of the magnetic therapeutic pad so as to improve the look and the durability of the magnetic therapeutic pad.

The substrate layer 30 is electrically insulating and can be made by Bakelite, plastic or other suitable material. The upper and lower surfaces of the substrate layer 30 may be smooth. The substrate layer 30 in this embodiment has a rectangular shape. It is understood that the substrate layer 30 may be of other shapes.

Figure 2:
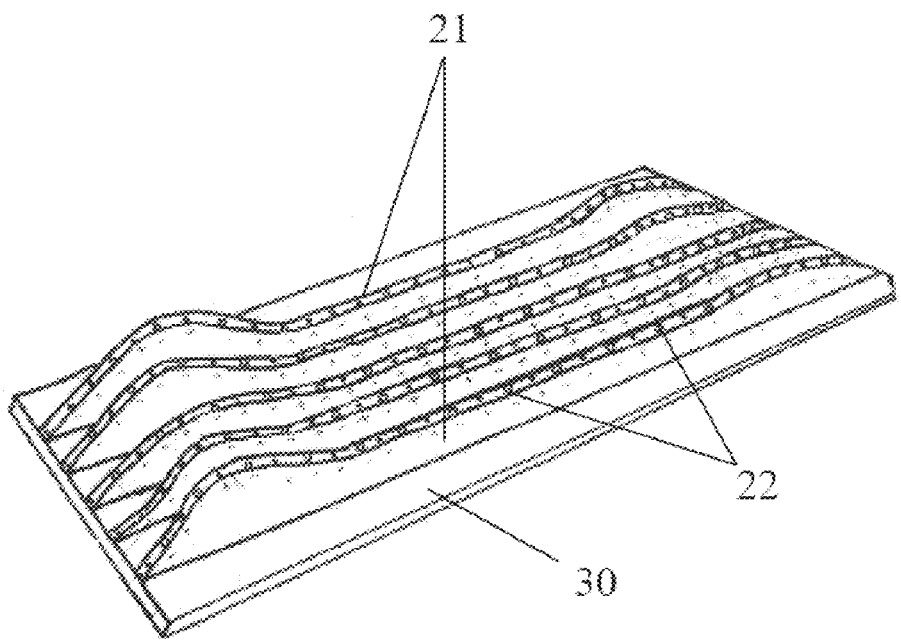
FIG. 2 illustrates the structure of a support layer of the magnetic therapeutic pad for a human spine depicted in FIG. 1.

FIG. 2 illustrates the structure of the support layer 20 of the magnetic therapeutic pad for a human spine in this embodiment. Referring to both FIG. 1 and FIG. 2, the support layer 20 is made by a rigid material, for example, insulating Bakelite or plastic, and is configured for supporting the weight of a user lying on the magnetic therapeutic pad. The support layer 20 includes multiple ridge frames 21 spaced with one another. The upper edges of the ridge frames 21 are protruding out from an upper surface of the substrate layer 30. The protruding upper edges of each ridge frame form a curvature that is compatible with the curvature of a human back. Multiple magnets 22 are respectively disposed at the upper edges of each ridge frame 21 and spaced from one another according to the human meridian system. The support layer 20 and the substrate layer 30 can be formed together by one-time injection molding or die molding, or alternatively be assembled together after being separately formed.

Figure 5:
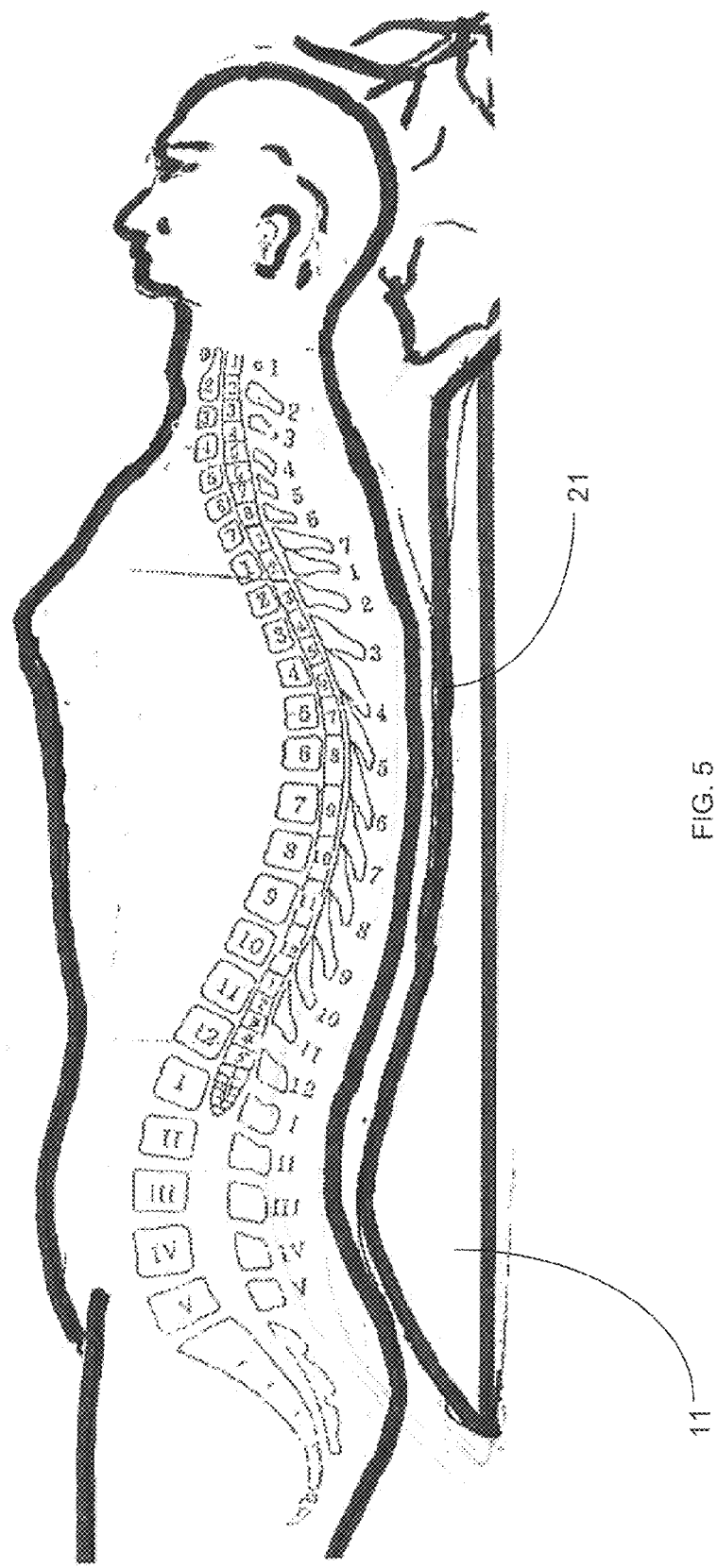
FIG. 5 illustrates a user lying on the magnetic therapeutic pad for a human spine depicted in FIG. 1 while the user's spine is being treated thereby.

In the illustrated embodiment, the buffer layer 10 can be made by rubber or Styrofoam with a proper toughness and about 1 cm thick. Being pasted and covered on the upper edges of the ridge frames 21, the buffer layer 10 is configured to reduce the uncomfortable feeling on a user's back caused by the support layer 20 when the person is lying on the magnetic therapeutic pad. Corresponding to the curvature of the upper edges of the ridge frames 21, the curvature of the upper surface of the buffer layer 10 matches with the curvature of a human back. As illustrated by FIG. 5, when a user is lying on the magnetic therapeutic pad, the back of the user is in tight contact with the upper surface of the buffer layer 10 (not shown in FIG. 5) so that the user's spine fits in between the ridge frames 21 and at the upper edges of ridge frames 21, and the spine of the user is thereby treated.

Figure 3:
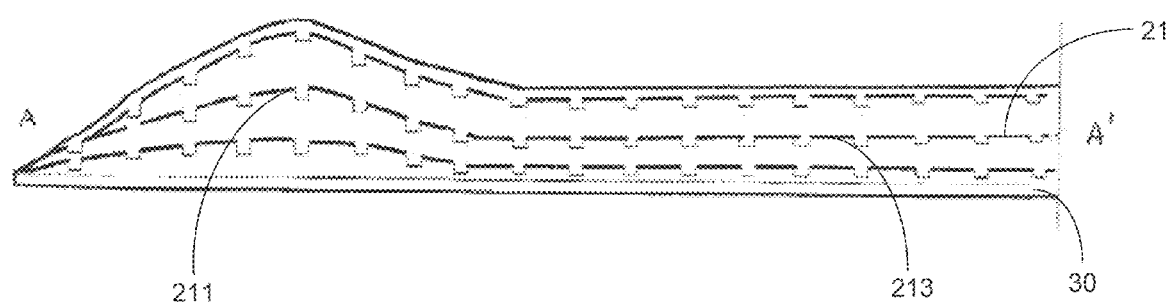
FIG. 3 is a cross-sectional view of the magnetic therapeutic pad for a human spine depicted in FIG. 1 taken along the line AA' in FIG. 1.
Figure 4:
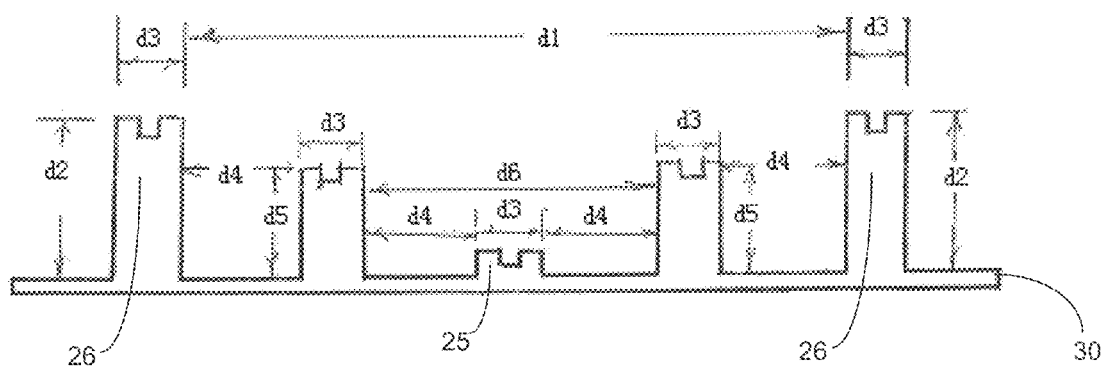
FIG. 4 is a cross-sectional view of the magnetic therapeutic pad for a human spine depicted in FIG. 1 taken along the line BB' in FIG. 1.

FIG. 3 and FIG. 4 are cross-sectional views of the magnetic therapeutic pad for a human spine depicted in FIG. 1 taken along the line AA' and the line BB' in FIG. 1 respectively. Referring to FIG. 3 and FIG. 4, the height of each ridge frame 21 of the support layer 20, which is the distance between the upper edge of the ridge frame 21 and the upper surface of the substrate layer 30, varies with different portions of the ridge frame, varies with different ridge frames at a same portion, and is configured to be compatible with the curvature of a human back.

Referring to FIG. 3, each ridge frame 21 includes a waist portion 211 and a neck-chest portion 213. The waist portion 211 and the neck-chest portion 213 correspond to the waist, neck-chest area of a human appropriately. The upper edges of the waist portion 211 of the ridge frame 21 forms a curvature, and the highest point of the upper edges of the waist portion 211 is the highest point of the whole ridge frame 21. The upper edges of the neck-chest portion 213 of the ridge frame form a line that is parallel to the upper surface of the substrate layer 30.

Referring to FIG. 4, the height of the ridge frame 25 at a center of the magnetic therapeutic pad (also called the center ridge frame) is the lowest among all the ridge frames and is about 1.5 cm to about 2 cm on average. An average height d5 of the ridge frames at the two sides of the center ridge frame is about 2 cm to about 4 cm higher than that of the center ridge frame. The two ridge frames at the outermost sides of the pad (the outermost ridge frames 26) are the highest among all the ridge frames with an average height d2 of about 4 cm to about 6 cm. The ridge frames 21 are spaced at a distance d4 of about 4 cm from one another. A width d3 of each ridge frame 21 is approximate to the width of human spinal vertebrae and is about 2 cm. A distance d1 between the two outermost ridge frames is about 22 cm. A distance d6 between the two ridge frames that are adjacent to the outermost ridge frames is about 10 cm.

FIG. 5 illustrates a user lying on the magnetic therapeutic pad 11 for a human spine depicted in FIG. 1 while the user's spine is being treated thereby. Referring to FIG. 5, the weight of the user pushes the spinous processes of the complete spine of the user in between the ridge frames 21 so as to correct scoliosis, spinal misalignment, vertebral deformity and other medical conditions that the user may have.

Figure 6:
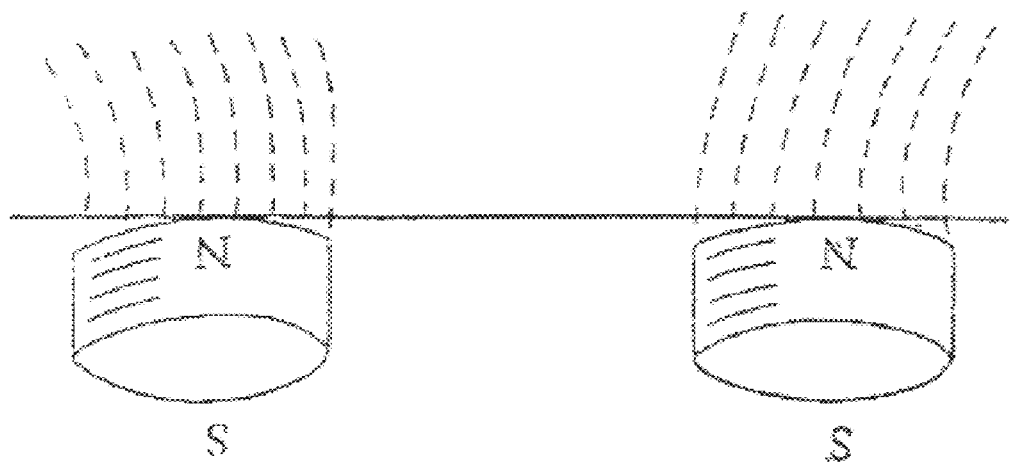
FIG. 6 illustrates a magnetic flux distribution near two magnetic poles of the same polarity being placed in the proximity to each other.
Figure 7:
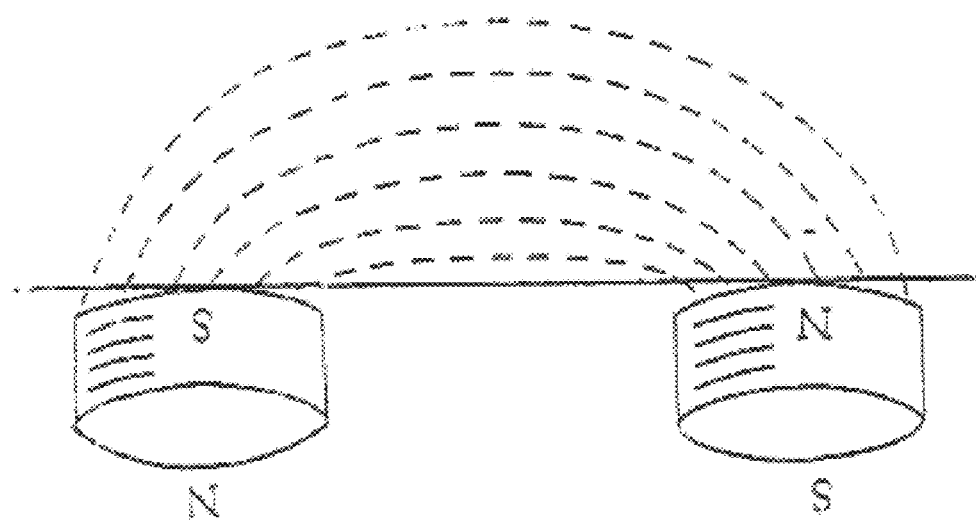
FIG. 7 illustrates a magnetic flux distribution near two magnetic poles of opposite polarities being placed in the proximity to each other.

FIG. 6 illustrates a magnetic flux distribution near two magnetic poles of the same polarity being placed in the proximity to each other. It is shown in FIG. 6 that there is essentially no magnetic flux between the two magnetic poles. FIG. 7 illustrates a magnetic flux distribution near two magnetic poles of opposite polarities being placed in the proximity to each other. It is shown in FIG. 7 that the density of the magnetic fluxes between the two magnetic poles in this case is relative high. To maximize the therapeutic effects of the magnetic field, in this embodiment, magnets with opposite polarities are arranged next to each other along the same meridian so that the meridian is under the effect of continuous magnetic fluxes.

More specifically, referring back to FIG. 2, in this embodiment the support layer 20 includes five ridge frames 21. The five ridge frames, respectively corresponding to five different human meridians, are arranged and fixed on the substrate layer 30 in a way that the ridge frames extend from the substrate layer 30 to form projections. The projections have outer edges and are parallel to each other. Among the five ridge frames, the center ridge frame corresponds to the Governor meridian (Du meridian) on a human's back, the two outermost ridge frames correspond to the outer Urinary Bladder meridians on a human's back, and the two ridge frames between the center ridge frame and the outermost ridge frames correspond to the inner Urinary Bladder meridians on a human's back. The average distance between the neighboring protruding upper edges of each ridge frame is about 3 cm to about 5 cm, and the protruding upper edges of each ridge frame respectively match the acupuncture points on the meridian that the ridge frame corresponds to when a user is lying on the magnetic therapeutic pad.

According to the traditional Chinese medicine, the Governor meridian (Du meridian) runs on the spinal column. The two inner Urinary Bladder meridians run next to and along each side of the Governor meridian (Du meridian). The two outer Urinary Bladder meridians respectively run next to the inner Urinary Bladder meridians along the sides thereof that are away from the Governor meridian (Du meridian). The Governor meridian (Du meridian), the inner Urinary Bladder meridians, and the outer Urinary Bladder meridians together perform a vital function in regulation, nourishment and therapy of the organs of the entire human body and in maintaining the person's general health. Acupuncture points, also called acupoints, are locations on the body that are the focus of acupuncture, acupressure, sonopuncture and laser acupuncture treatment. Several hundred acupuncture points are located along meridians (connected points across the anatomy which affect a specific organ or other part of the body).

Figure 8:
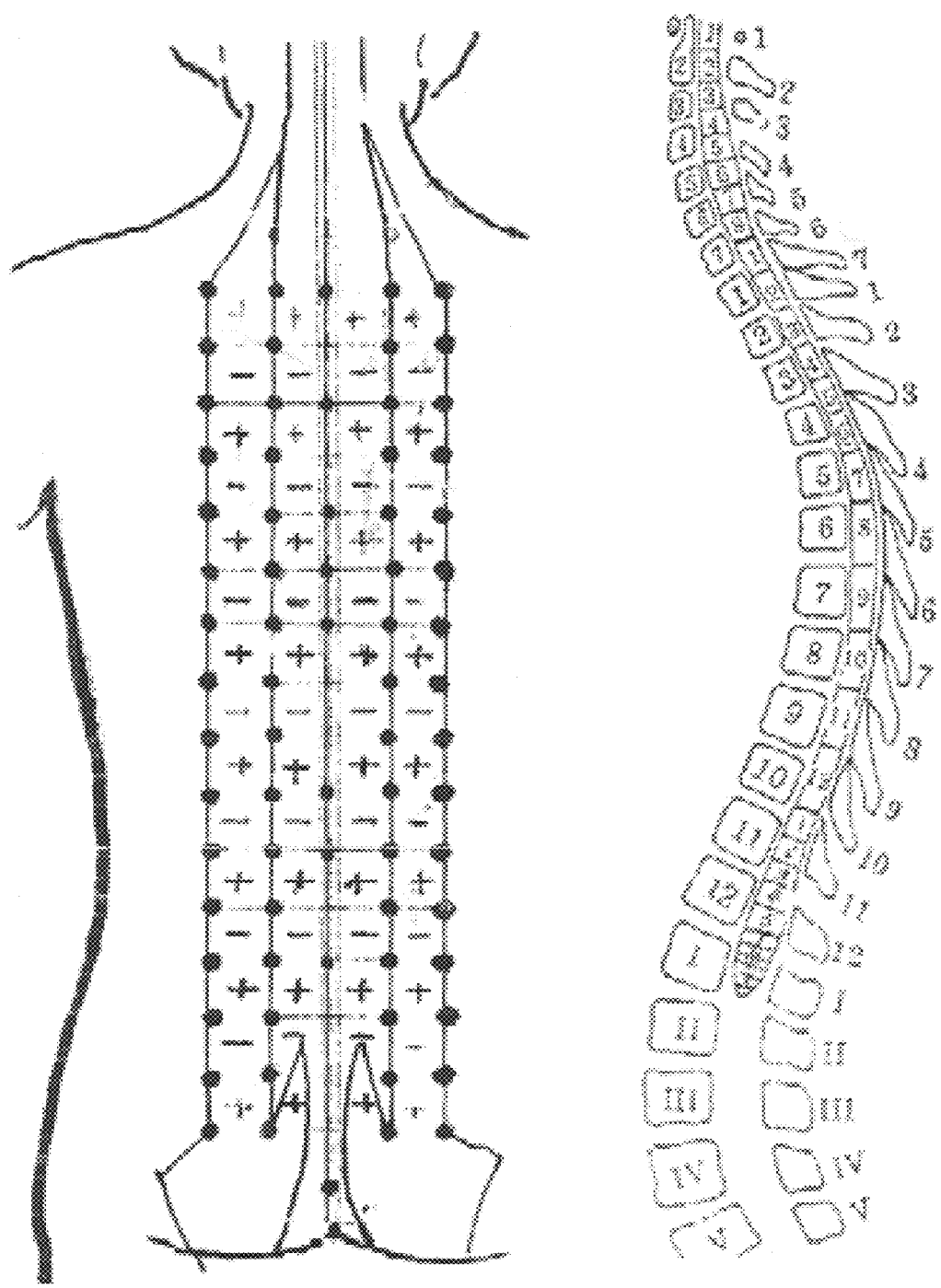
FIG. 8 illustrates the polarity arrangement of multiple magnets in the magnetic therapeutic pad for a human spine depicted in FIG. 1.

FIG. 8 illustrates the polarity arrangement of the multiple magnets in the magnetic therapeutic pad for a human spine in this embodiment. Referring to both FIG. 2 and FIG. 8, a circular hole is formed at each protruding upper edge of each ridge frame and a permanent magnet 22 is disposed in each hole. In this embodiment, the neighboring magnets on the same ridge frame 21 have opposite polarities. In other words, N and S polarities are arranged on each ridge frame 21 in an alternating fashion. Continuous magnetic fluxes are thus formed throughout the whole ridge frames 21 so that qi (energy flow in the human body) and blood circulation along the corresponding meridians on the back of the user lying on the ridge frames 21 can be enhanced by the continuous magnetic fields.

Referring to FIG. 8, to avoid interference between magnets on the neighboring ridge frames, the magnets along a line perpendicular to the ridge frames 21 are arranged to have the same polarity. Based on the illustration in FIG. 6, the magnetic interference between magnets of the same polarity on the neighboring ridge frames is minimal.

To accommodate users of different body sizes, the magnetic therapeutic pad for a human spine in this embodiment can be made into different sizes. A magnetic therapeutic pad for a human spine of a regular size is about 50-100 cm long and about 20-40 cm wide. It is understood that the spacing between neighboring ridge frames 21, namely d4 as illustrated in FIG. 4, may vary for the magnetic therapeutic pads of different sizes, for example, ranging from about 3 cm to about 5 cm.

When being used, the magnetic therapeutic pad for a human spine is first laid on a bed. When a user lies down, he or she may place his or her bottom close to the waist portion end of the magnetic therapeutic pad first. Then he or she may lay himself or herself onto the magnetic therapeutic pad and adjust his or her back and waist to a comfortable position. The user may lie on the magnetic therapeutic pad 11 for 20-30 minutes as illustrated in FIG. 5. It is noted that the user should be advised not to lie on the magnetic therapeutic pad for over 30 minutes.

In this embodiment, the continuous magnetic fluxes throughout the user's meridians are capable of invigorating and revitalizing the qi (energy flow) of the entire meridians. As a result, the general health of the user may be improved. Pains and other discomforts of the user may be reduced or relieved, especially when the magnetic therapeutic pad with a human spine compatible curvature provides the user with a suitable back support. In addition, the weight of the user is utilized in this embodiment to enhance the stimulation of the acupuncture points and the meridians when the user is lying on the magnetic therapeutic pad.

It has been proved that the magnetic therapeutic pad for a human spine in this embodiment is capable of producing analgesic, anti-inflammatory and sedative effects, reducing swelling and lowering blood pressure for the user. Furthermore, the magnetic therapeutic pad for a human spine has chiropractic functions and has been proved to be very effective in treating acute lumbar sprain and vertebral displacement, not only in terms of shortening the course of treatment, but also in terms of immediate effects. In a random sample of 10 back pain patients and 10 spine disease patients, the curing effects of the magnetic therapeutic pad for a human spine is shown as in Table 1:

TABLE 1

| Effects | 10 back pain patients | Cure rate | 10 spine disease patients | Cure rate |
|---|---|---|---|---|
| Cured after one treatment | 3 people | 30% | 7 people | 70% |
| Cured after ten treatments | 5 people | 50% | 8 people | 80% |

It has been observed that after a patient lies on the magnetic therapeutic pad for a human spine for one minute, the skin temperature of the Shenzhu point (an acupuncture point) on the patient's back increases from 25-28.degree. C. to 29-30.degree. C. 20 minutes later, the temperature increases to 30-35.degree. C. The skin temperature of the Mingmen point (another acupuncture point) on the patient's waist increases from 28-30.degree. C. before the patient's lying on the magnetic therapeutic pad to 36.degree. C. after so. Hence, it is proved that under the influence of the magnetic fluxes provided by the magnetic therapeutic pad for a human spine of this embodiment, the circulation of qi (energy flow) and blood along the meridians is enhanced, nerve relaxation is facilitated, analgesic effects and health recovering results are improved, and the purposes of chiropractic therapy are effectively achieved. The test results for acupuncture point temperature change of patients lying on the magnetic therapeutic pad for a human spine in this embodiment are shown in Table 2.

TABLE 2

| Room Temperature (° C.) | Skin Temperature of Shenzhu Point (° C.) | | | Skin Temperature of Mingmen Point (° C.) | | | |
|---|---|---|---|---|---|---|---|
| | Before lying on the magnetic therapeutic pad | After lying on the magnetic therapeutic pad | | Before lying on the magnetic therapeutic pad | After lying on the magnetic therapeutic pad | | |
| 22° C. | 28-30° C. | 5-10 minutes 30-32° C. | 20 minutes 30-35° C. | 28-30° C. | 5-10 minutes 30-33° C. | 20 minutes 33-35° C. | 30 minutes 35-36° C. |

In Table 2, Shenzhu point refers to an acupuncture point on the lower back below the spinous process of the third thoracic vertebra (T3), and Mingmen point refers to an acupuncture point on the lower back below the spinous process of the second lumbar vertebra (L2). Similar to the locations of the human meridians, the locations of these acupuncture points are well known in the art.

While the present patent application has been shown and described with particular references to a number of embodiments thereof, it should be noted that various other changes or modifications may be made without departing from the scope of the present invention.

The invention claimed is:

1. A magnetic therapeutic pad for a human spine comprising:
   a substrate layer;
   a support layer above the substrate layer, the support layer comprising five ridge frames spacing at distance from one another and adapted to extend generally parallel to the human spine, each of the five ridge frames being constructed of a board, upper edges of the boards being curved and protruding out from an upper surface of the substrate layer; wherein each board is continuous along the length of the pad;
   a buffer layer covers on the support layer; and
   a plurality of magnets disposed on the upper edges of the ridge frames according to the human meridian system; wherein:
   the five ridge frames respectively correspond to a Governor meridian, inner Urinary Bladder meridians, and outer Urinary Bladder meridians on a human's back;
   the upper edges of each ridge frame form a curvature that is compatible with a curvature of a human back;
   the magnets respectively match acupuncture points on the meridians that the ridge frames correspond to when a user is lying on the magnetic therapeutic pad; and
   each of the magnets are disposed in a hole formed at the protruding upper edge of each ridge frame; wherein
   N and S polarities of the magnets are arranged on each of the ridge frames in an alternating fashion so that any two neighboring magnets on each continuous board of the ridge frames have opposite polarities without a valley therebetween; and
   the magnets along a line perpendicular to the ridge frames have the same polarity in a symmetrical fashion.

2. The magnetic therapeutic pad for a human spine of claim 1, wherein an average distance between the neighboring protruding upper edges of each ridge frame is about 3 cm to about 5 cm, and a width of each ridge frame is approximate to a width of human spinal vertebrae.

3. The magnetic therapeutic pad for a human spine of claim 1, wherein each ridge frame comprises a waist portion and a neck-chest portion, a highest point of the upper edges of the waist portion is the highest point of the whole ridge frame, and the upper edges of the neck-chest portion of the ridge frame form lines that are parallel to an upper surface of the substrate layer facing the support layer.

4. The magnetic therapeutic pad for a human spine of claim 1, the height of the ridge frame at a center of the therapeutic pad is the lowest among all the ridge frames, the height of the ridge frames gradually increases from the center ridge frame toward the ridge frames at outer sides of the pad, and the heights of the ridge frames at outermost sides of the pad are the highest among all of the ridge frames.

5. The magnetic therapeutic pad for a human spine of claim 1, wherein the ridge frames are arranged and fixed on the substrate layer in a way that the ridge frames extend from the substrate layer to form projections, wherein the projections have outer edges and are parallel to each other; and the distance between the neighboring ridge frames ranges from about 3 cm to about 5 cm.

6. A magnetic therapeutic pad for a human spine comprising:
   a substrate layer;
   a support layer above the substrate layer, the support layer comprising five ridge frames spacing at a distance from one another and extending adapted to extend generally parallel to the human spine, each of the five ridge frames being constructed of a board, upper edges of the board being curved and protruding out from an upper surface of the substrate layer; wherein each board is continuous along the length of the pad;
   a plurality of magnets disposed on the upper edges of the ridge frames according to the human meridian system; wherein:
   the five ridge frames respectively correspond to a Governor meridian, inner Urinary Bladder meridians, and outer Urinary Bladder meridians on a human's back; and
   the upper edge of each ridge frame forms a curvature that is compatible with a curvature of a human back;
   the magnets respectively match acupuncture points on the meridians that the ridge frames correspond to when a user is lying on the magnetic therapeutic pad;
   N and S polarities of the magnets are arranged on each of the ridge frames in an alternating fashion so that any two neighboring magnets on each continuous board of the ridge frames have opposite polarities without a valley therebetween; and
   the magnets along a line perpendicular to the ridge frames have the same polarity in a symmetrical fashion.

7. The magnetic therapeutic pad for a human spine of claim 6, wherein the average distance between the neighboring protruding upper edges of each ridge frame is about 3 cm to about 5 cm, and a width of each ridge frame is approximate to the width of human spinal vertebrae.

8. The magnetic therapeutic pad for a human spine of claim 6, wherein each ridge frame comprises a waist portion and a neck-chest portion, a highest point of the upper edges of the waist portion is the highest point of the whole ridge frame, and the upper edges of the neck-chest portion of the ridge frame form lines that are parallel to an upper surface of the substrate layer facing the support layer.

9. The magnetic therapeutic pad for a human spine of claim 6, the height of the ridge frame at a center of the pad is the lowest among all the ridge frames, the height of the ridge frames gradually increases from the center ridge frame toward the ridge frames at outer sides of the pad, and the heights of the ridge frames at outermost sides of the pad are the highest among all of the ridge frames.

10. The magnetic therapeutic pad for a human spine of claim 6, wherein the ridge frames are arranged and fixed on the substrate layer in a way that the ridge frames extend from the substrate layer to form projections, wherein the projections have outer edges and are parallel to each other; and the distance between the neighboring ridge frames ranges from about 3 cm to about 5 cm.

11. A magnetic therapeutic pad for a human spine comprising:
 a substrate layer;
 a support layer above the substrate layer, the support layer comprising five ridge frames spacing at a distance from one another and adapted to extend generally parallel to the human spine, each of the five ridge frames being constructed of a board, upper edges of the board being curved and protruding out from an upper surface of the substrate layer; wherein each board is continuous along the length of the pad;
 a plurality of magnets disposed on the upper edges of the ridge frames according to the human meridian system; wherein:
 the five ridge frames respectively correspond to a Governor meridian, inner Urinary Bladder meridians, and outer Urinary Bladder meridians on a human's back;
 the upper edges of the ridge frames form a curvature that is compatible with a curvature of a human back;
 N and S polarities of the magnets are arranged on each of the ridge frames in an alternating fashion so that any two neighboring magnets on each continuous board of the ridge frames have opposite polarities without a valley therebetween; and
 the magnets along a line perpendicular to the ridge frames have the same polarity in a symmetrical fashion.

12. The magnetic therapeutic pad for a human spine of claim 11, wherein the average distance between the neighboring protruding upper edges of each ridge frame is about 3 cm to about 5 cm, and a width of each ridge frame is approximate to the width of human spinal vertebrae.

13. The magnetic therapeutic pad for a human spine of claim 11, wherein each ridge frame comprises a waist portion and a neck-chest portion, a highest point of the upper edges of the waist portion is the highest point of the whole ridge frame, and the upper edges of the neck-chest portion of the ridge frame form lines that are parallel to an upper surface of the substrate layer facing the support layer.

14. The magnetic therapeutic pad for a human spine of claim 11, the height of the ridge frame at a center of the pad is the lowest among all the ridge frames, the height of the ridge frame gradually increases from the center ridge frame toward the ridge frames at outer sides of the pad, and the heights of the ridge frames at outermost sides of the pad are the highest among all of the ridge frames.

15. The magnetic therapeutic pad for a human spine of claim 11, wherein the ridge frames are arranged and fixed on the substrate layer in a way that their projections on the substrate layer are parallel to each other and the distance between the neighboring ridge frames ranges from about 3 cm to about 5 cm.

\* \* \* \* \*